April 25, 1972 R. S. MOORE Plant Pat. 3,137
MINIATURE ROSE PLANT
Filed Sept. 2, 1969
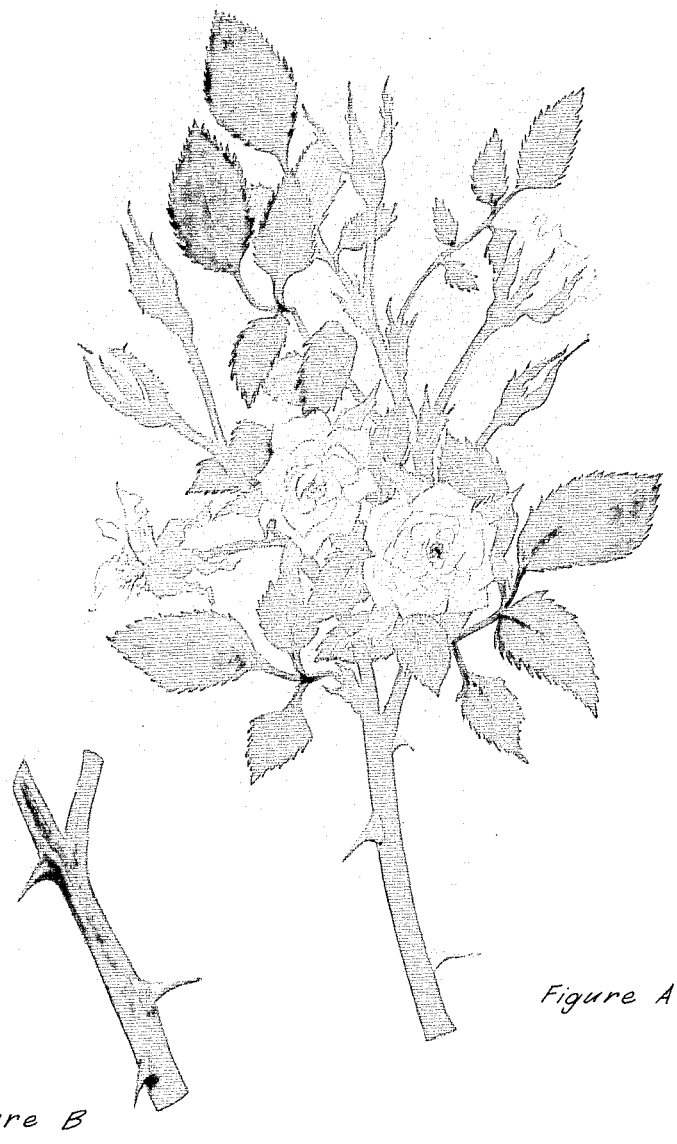
Figure A
Figure B
WITNESS
Jeanette Nunn Copley
INVENTOR
Ralph S. Moore United States Patent Office Plant Pat. 3,137
Patented Apr. 25, 1972

3,137
MINIATURE ROSE PLANT

Ralph S. Moore, 2519 E. Noble Ave.,
Visalia, Calif. 93277

Filed Sept. 2, 1969, Ser. No. 854,806
Int. Cl. A01h *5/00*
U.S. Cl. Plt.—9 1 Claim The present invention relates to a new and distinct variety of hardy, dwarf, bush type rose plant of the miniature class; the variety being primarily characterized—as to novelty—by rose pink buds and flowers which in general color effect are deep pink with an undertone of yellow or coral.

The variety is further characterized by:

An abundance of bloom, with flowers borne singly or several to stem.

Little or no fragrance.

A plant which is vigorous, of rounded upright shape, and with glossy, small foliage with pointed leaflets; the flowers and foliage being similar in form to the variety Yellow Doll (United States Plant Patent No. 2,450) but more compact and dwarf in plant habit with buds and flowers rose pink to light red in color, smaller size and less petals. The plant which has a normal average height of about 12" at maturity can be easily maintained at 10" or less by occasional trimming.

A plant which grows and blooms satisfactorily both in greenhouse and outdoors; is a good plant for growing in pots; and provides excellent garden decoration as well as cut flowers.

The present variety of miniature rose was originated by me at my nursery located at Visalia, Calif., under conditions of careful control and observation, as a cross between Little Darling, a fluoribunda (U.S. Plant Patent No. 1,581), as the seed parent and Magic Wand, a miniature (not patented), as the pollen parent.

Subsequent to origination of the variety I successfully asexually reproduced it, in my nursery located as aforesaid, by budding as well as by cuttings; the reproductions having run true in all respects.

The figure of the drawing illustrates a spray, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color identification are employed.

Type: Hardy; dwarf; bush; seeding; greenhouse; outdoors; garden decoration; potted plant.

Class: Miniature.

Flowers:

*Continuity.*—Continuous; repeat blooms all season.

*Fragrance.*—Little or none.

Flowers borne: Singly and several together on short, thin but sturdy, wire-like stem.

Quantity of bloom: Abundance; average or above both outside and inside greenhouse.

Bud:

Peduncle.—Short, about ¾" to 1"; slender but sturdy; erect; medium green—often bronze outdoors; numerous tiny soft hairs. Before calyx breaks—size—small. From.—long; pointed, usually without leafy appendages on surface of bud; but with numerous very short hairs on sepals with foliaceuos parts extending beyond the tip of the bud equal to less than ¼ of its length. Color—medium green (often bronze outdoors). As calyx breaks—color—deep pink. As first petal opens—deep rose pink with soft understone of coral; size—small. Color—outside—Crimson 22/2 shading deeper on lower ½ of petal, with pale green-yellow base; inside—Crimson 22/1 or slightly darker with pale green-yellow base.

*Form.*—Medium long; pointed.

*Openings.*—Usually opens well in all weather.

Bloom:

*Size when fully open.*—Small, averaging 1¼" or slightly smaller.

*Petalage.*—Double—about 23–30 petals; usually with no or very few, narrow petaloids.

*Form.*—Silghtly cupped, moderately full at first; with petals rolled loosely outward, and later at maturity petals rolled outward with stamens showing.

Petals: Fairly thick, satinyl both inside and outside.

Shape—outside petals broad lanceolate with nearly round tip; intermediate—medium to broad lanceolate, nearly round tip; inside—lanceolate, rounded tip.

Color: Newly opened flower from a plant in greenhouse (late August 1969), Visalia, Calif. (Opening bud and flower tends to be lighter color indoors during short days (winter) and may be darker color during normal (spring, summer and fall) growing season, both indoors and outdoors).

*Outside petal.*—Outside surface—Tyrian Rose 24/2, near white at base; inside surface—Tyrian Rose 24/1, pale yellow-green at base.

*Intermediate petal.*—Outside surface—Tyrian Rose 24/1, pale yellow-green at base; inside surface—Crimson 22/1, pale yellow-green at base.

*Inside petal.*—Same as intermediate petal. General color effect.—Newly opened flower—bright rose pink. Three days open—deep rose pink but without coral undertone. Behaviour—petals persist for a time. Flower longevity (May–June)—bush in garden 5 days or longer. Cut flowers kept at living room temperature—up to 7 days.

Reproductive organs:

*Stamens.*—Moderate amount; yellow.

*Anthers.*—Moderate amount; golden.

*Pollen.*—Sparse; usually none.

*Pistils.*—Moderate number.

*Styles.*—Even; short; very slender; pale green-white shading upward into red.

*Stigma.*—Well formed; pale pink to near white.

*Ovaries.*—All enclosed in calyx.

*Hips.*—None.

*Sepals.*—Spear shaped; remain tight against opening bud and turn down (recurved) as flower opens; usually drop off with peduncle.

*Seeds.*—None.

Foliage:

*Leaves.*—Compound of 5 (occasionally 3 or 7) leaflets—abundant, small, leathery, glossy.

*Leaflets.*—Shape—lanceolate; apex acute; base rounded (sometimes acute). Margin—serrate, Color: medium to dark green; new growth bronzy.

*Rachis.*—Medium strength; upper surface grooved with a few very tiny short prickles; under side—several small thorns and tiny prickles.

*Stipules.*—Short to medium length; narrow medium length points, turning out at an angle of about 45 degrees.

Growth:

*Habit.*—Dwarf, bushy; moderately spreading; much branched.

*Growth.*—Free; vigorous (very compact).

*Canes.*—Slender; medium.

*Main stems.*—Color: medium green. *Thorns*—moderately thorny; small oval base; medium length; straight (not hooked). Color—gray—brown. *Prickles*—none. *Hairs*—none.

*Branches.*—Color—medium green. *Thorns*—moderately thorny; medium length; straight. Color—brownish.

*New Shoots.*—Color—medium green, sometimes lightly tinted reddish. *Thorns.*—moderately thorny; medium length; straight; short oval base. Color—reddish. *Prickles*—none. *Hairs*—none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, rounded, much branched, bush type, as illustrated and described, characterized by buds and flowers resembling in form the Yellow Doll (Plant Patent No. 2,450) miniature rose with the flower color being shades of rose pink or light red, resembling Pixie Rose (Patent No. 2,095) miniature rose in this respect, the buds and flowers generally smaller and with less petals than Yellow Doll; and further characterized by a plant which is vigorous and compact, easy to propagate from cuttings, with reddish or bronze colored new shoots and foliage, with small deep green glossy mature foliage and an abundance of bloom, with flowers born singly or several to the stem in loose clusters.

No references cited.

ROBERT E. BAGWILL, Primary Examiner